United States Patent [19]

Rothgery

[11] Patent Number: 5,039,816

[45] Date of Patent: Aug. 13, 1991

[54] PROCESS FOR THE PRODUCTION OF 1,2,4-TRIAZOL-5-ONE

[75] Inventor: Eugene F. Rothgery, North Branford, Conn.

[73] Assignee: Olin Corporation, Cheshire, Conn.

[21] Appl. No.: 572,593

[22] Filed: Aug. 27, 1990

[51] Int. Cl.$^5$ ............................................. C07D 249/12
[52] U.S. Cl. .................................................. 548/263.2
[58] Field of Search ..................................... 548/263.2

[56] References Cited

U.S. PATENT DOCUMENTS 4,482,738  11/1984  Rothgery .............................. 564/37
4,733,610   3/1988  Lee et al. ............................ 102/332

FOREIGN PATENT DOCUMENTS 0210881  4/1987  European Pat. Off. .

*Primary Examiner*—Mary C. Lee
*Assistant Examiner*—Patricia L. Morris
*Attorney, Agent, or Firm*—Dale Lynn Carlson

[57] ABSTRACT

A process for producing chloride ion-free 1,2,4-triazol-5-one which comprises: a) heating a mixture of hydrazodicarbonamide and formic acid to a reflux temperature for said mixture, b) refluxing said mixture at said reflux temperature for a time sufficient to cause said mixture to change its visual appearance from a cloudy mixture to a clear solution, and c) removing unreacted formic acid from said clear solution to provide the desired 1,2,4-triazol-5-one product free of chloride ion.

5 Claims, No Drawings

PROCESS FOR THE PRODUCTION OF 1,2,4-TRIAZOL-5-ONE

FIELD OF THE INVENTION

This invention relates to a process for the production of triazolone compounds. More particularly, the invention relates to a process for the production of 1,2,4-triazol-5-one free of chloride ion.

BACKGROUND OF THE INVENTION 1,2,4-Triazol-5-one (or its tautomeric form; 5-hydroxy-1H-1,2,4-triazole) is a known compound, commonly referred to as "TO" and useful as an intermediate in the production of explosives which are relatively insensitive to shock, impact, and friction, and in the synthesis of dyestuffs. In practice, the TO intermediate is nitrated to produce 3-nitro-1,2,4-triazol-5-one which is used in explosive compositions. The presence of chloride ion concentrations in TO is undesirable since the presence of chloride ion stored in explosives results in increased corrosion of the casings and unwanted gas formation.

Unfortunately, prior art processes for the production of TO have generally utilized semicarbazide hydrochloride as a reactant resulting in the presence of the unwanted chloride ion in the TO product. By way of illustration, European Patent Application 0 210 881, published Apr. 2, 1987 in the name of Becuwe, discloses a process for preparing 1,2,4-triazol-5-one in which formic acid is pre-heated to 70°-75° C. and semicarbazide hydrochloride added to form a reaction mixture. The reaction mixture is then heated to produce a product which is subsequently evaporated to dryness. As another illustration, U.S. Pat. No. 4,733,610, issued Mar. 29, 1988 to K-Y Lee et al discloses a process for preparing 1,2,4-triazol-5-one in which a mixture of semicarbazide hydrochloride and formic acid is heated, and then concentrated by distillation of excess formic acid until the desired product crystallizes.

Heretofore, processes for making TO without the use of a chloride-containing reactant have not been known to the knowledge of the present inventor. New processes which do not utilize a chloride-containing reactant and which produce a chloride ion-free TO product would be highly desired by the NTO manufacturing industry.

SUMMARY OF THE INVENTION

In one aspect, the present invention relates to a process for producing chloride ion-free 1,2,4-triazol-5-one which comprises:

a) heating a mixture of hydrazodicarbonamide and formic acid to a reflux temperature for said mixture, b) refluxing said mixture at said reflux temperature for a time sufficient to cause said mixture to change its visual appearance from a cloudy mixture to a clear solution.

c) removing unreacted formic acid from said clear solution to provide the desired 1,2,4-triazol-5-one product free of chloride ion.

This and other aspects will become apparent upon reading the following detailed description of the invention.

DETAILED DESCRIPTION OF THE INVENTION

In accordance with the present invention, a new route to produce 1,2,4-triazol-3-one has been discovered which comprises refluxing hydrazodicarbonamide ("HDCA") in formic acid until a clear solution results. One advantage associated with the process of the present invention is the visually observable change from a cloudy reaction mixture to a clear product solution upon completion reaction which provides a simple indicator of the desired TO formation.

According to the process of the present invention, HDCA is reacted with formic acid in a ring-forming or cyclization reaction required to produce the 1,2,4-triazol-5-one. The HDCA reactant is typically produced as a heretofore undesirable byproduct of the reaction of hydrazine with urea and hydrogen chloride to obtain semicarbazide hydrochloride as described in U.S. Pat. No. 4,482,738, issued Nov. 13, 1984 to E. F. Rothgery. Indeed, in the past great care was taken to remove all HDCA from the semicarbazide hydrochloride prior to the reaction of the latter with formic acid.

To conduct the process of the invention, the HDCA and the formic acid are heated to reflux temperature to produce a product mixture containing the desired TO product. While the reaction is preferably conducted at about atmospheric pressure, greater than atmospheric pressures may be employed if desired. The reaction time utilized can vary up to several hours or more, depending upon the amount of formic acid employed. Without wishing to be bound by any particular theory, this dependency is apparently due to the low solubility of HDCA. The weight ratio of formic acid to HDCA employed is preferably between about 3:1 and about 15:1, more preferably between about 5:1 and about 10:1.

After the reaction is complete, the temperature is preferably increased in order to strip off the formic acid. After essentially all of the formic acid has been removed, cooling of the product is preferably effected in order to facilitate crystallization of the 1,2,4-triazol-5-one. The crystals are separated from the mother liquor, and are washed, preferably with water.

If desired, recrystallization of the 1,2,4-triazol-5-one crystals is carried out, for example, by slurrying the crystals in water, heating the slurry to solubilize the 1,2,4-triazol-5-one crystals, and cooling the slurry to form crystals of 1,2,4-triazol-5-one of a higher purity. The supernatant liquor which contains solubilized triazolone is removed and may be recycled to the formic acid stripping step. The recrystallization step may be repeated if desired.

1,2,4-Triazol-5-one crystals produced by the novel process of the invention are highly pure and are free of any detectable chloride ions. The TO product will not result in corrosion when used in castable explosives such as 3-nitro-1,2,4-triazol-5-one. These crystals may be dried or further reacted to produce any desired derivative.

Thus, the novel process of the present invention results in high yields of high purity TO that is free of chloride ion. In addition, the process, which can be operated continuously, generates effluents which, after neutralization, can be readily disposed of in public waterways.

The following examples further illustrate the novel process of the invention without any intention of being limited thereby. All parts and percentages are by weight unless otherwise specified. All patents and patent applications referred to herein are incorporated herein by reference in their entirety.

EXAMPLE 1

Preparation of TO Product

HDCA (11.8 g, 0.1 mole) was slurried in 96% formic acid (69 g) and heated to reflux. After 13 hours a clear, colorless solution resulted. The majority of the formic acid was removed under vacuum, leaving a wet, white solid. The product was slurried with 60 ml of methanol, filtered and washed with an additional 40 ml. Obtained was 6 g of solid melting at 225°–227° C., a 70% yield. The infra-red spectrum matched that of an authentic sample.

EXAMPLE 2

Another Preparation of TO Product

HDCA (12 g, 0.1 mole) was slurried in 80 ml of 96% formic acid and refluxed until a clear solution resulted. This required 20.5 hours. The excess formic acid was removed by vacuum stripping, leaving a white solid. Water (17 ml) was added and the mixture heated, on cooling the product crystallized. After filtering and drying, 4.6 g of product, a 54.6% yield of product was obtained.

Elemental analysis: Calc: C,28.24; H,3.55; N,49.40. Found: C,28.05; H,3.50; N,49.45.

Typical chlorine analyses for products obtained from this reaction have been less than 30 ppm, the limit of detection for the method used (X-ray fluorscence).

EXAMPLE 3

Another Preparation of TO Product

HDCA (29.5 g, 0.25 mole) was slurried in 312 ml of 96% formic acid and heated to reflux. The temperature was at the reflux point of formic acid (101° C.) initially, and slowly rose to 110° C. by the end of the reaction. After 3.75 hours a clear solution resulted. The excess formic acid was removed by vacuum stripping leaving a white solid. This material was slurried in 20 ml of water and filtered. The filter cake was washed with an additional 20 ml of water and dried to give 14.8 g of product, a 70% yield, melting at 215°–218° C.

What is claimed is:

1. A process for producing chloride ion-free 1,2,4-triazol-5-one which comprises:
   a) heating a mixture of hydrazodicarbonamide and formic acid to a reflux temperature for said mixture,
   b) refluxing said mixture at said reflux temperature for a time sufficient to cause said mixture to change its visual appearance from a cloudy mixture to a clear solution, and
   c) removing unreacted formic acid from said clear solution to provide the desired 1,2,4-triazol-5-one product free of chloride ion.

2. The process of claim 1 wherein the weight ratio of formic acid to hydrazodicarbonamide employed is between about 3:1 and about 15:1.

3. The process of claim 1 wherein the weight ratio of formic acid to hydrazodicarbonamide employed is between about 5:1 and about 10:1.

4. The process of claim 1 which is carried out at atmospheric pressure.

5. The chloride ion free product produced by the process of claim 1.

* * * * *